United States Patent [19]

Brown

[11] 4,203,918

[45] May 20, 1980

[54] HALO-SUBSTITUTED BENZOSPIRO CYCLOPROPANE CARBOXYLATES AS INSECTICIDES AND IXODICIDES

[75] Inventor: Dale G. Brown, Hopewell, N.J.

[73] Assignee: American Cyanamid Company, Stamford, Conn.

[21] Appl. No.: 926,990

[22] Filed: Jul. 21, 1978

[51] Int. Cl.² .................... C07C 120/00; C07C 67/00; A01N 9/20
[52] U.S. Cl. .................................. 260/465 D; 560/8; 424/304; 424/305
[58] Field of Search ................ 424/304, 305; 560/124, 560/8

[56] References Cited

U.S. PATENT DOCUMENTS

| | | | |
|---|---|---|---|
| 3,962,458 | 6/1976 | Schrider | 424/304 |
| 3,966,959 | 6/1976 | Addor | 424/304 |
| 3,981,903 | 9/1976 | Hirano et al. | 560/124 |
| 4,000,181 | 12/1976 | Elliot et al. | 424/304 |
| 4,001,428 | 1/1977 | Kosower et al. | 560/124 |
| 4,060,632 | 11/1977 | Addor | 424/304 |
| 4,072,752 | 2/1978 | Farooq et al. | 424/304 |
| 4,078,080 | 3/1978 | Schrider | 424/304 |
| 4,087,523 | 5/1978 | Lovell | 424/304 X |

*Primary Examiner*—Joseph P. Brust
*Attorney, Agent, or Firm*—H. G. Jackson

[57] ABSTRACT

The invention is novel halo-substituted benzospiro cyclopropane carboxylates useful for the control of insect pests of agriculturally important crops, and useful as insecticidal and acaricidal agents for the treatment of livestock and domestic animals.

1 Claim, No Drawings

HALO-SUBSTITUTED BENZOSPIRO CYCLOPROPANE CARBOXYLATES AS INSECTICIDES AND IXODICIDES

The invention is novel insecticidal-acaricidal pyrethroids of formula:

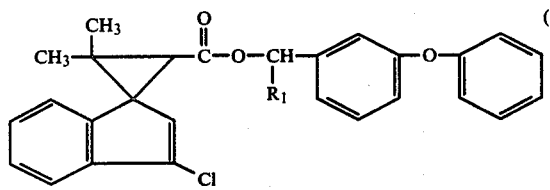
(I)

wherein $R_1$ is hydrogen or cyano, and the optical and geometric isomers thereof.

It is recognized, of course, that these isomers will vary somewhat in the degree of insecticidal and acaricidal activity which they exhibit towards a given pest; however, they are useful as insecticidal and/or acaricidal agents.

The invention also relates to a method for the control of insect pests of agronomic crops and of ectoparasites, especially ixodide ticks, of livestock and domestic animals.

Conveniently, the compounds of formula (I) may be prepared by the following reaction sequence:

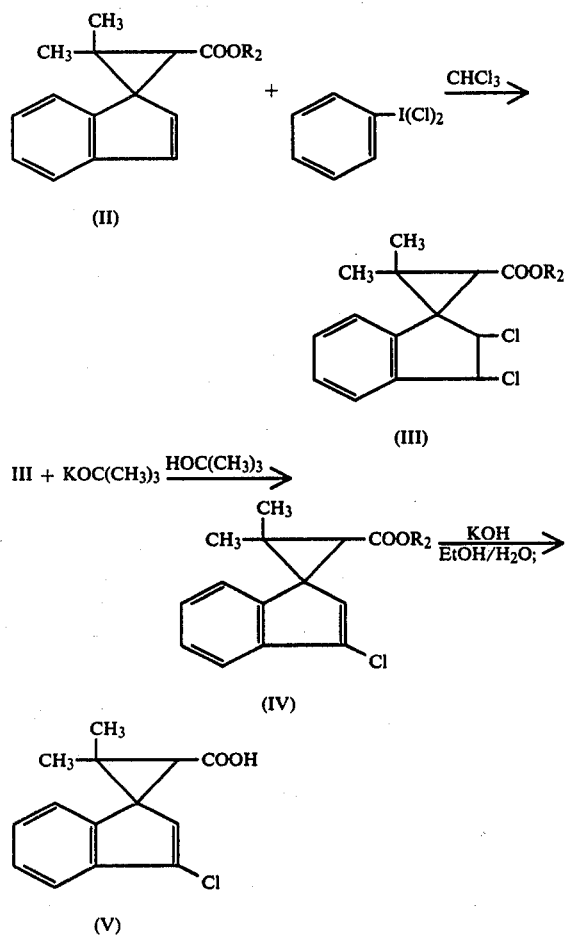

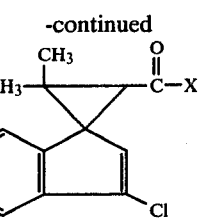
(VI)

and

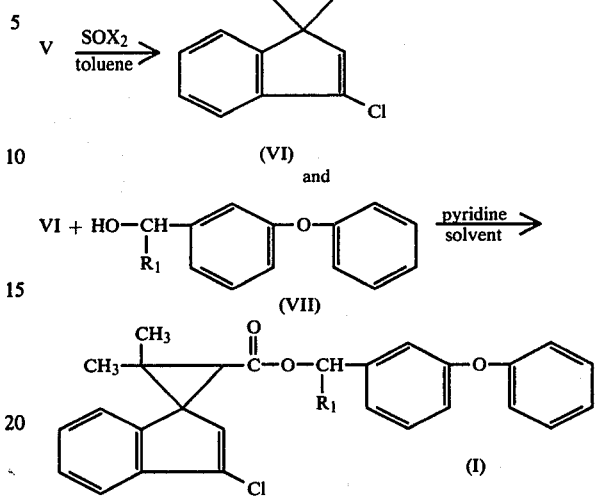
(I)

wherein $R_1$ is as hereinabove defined; $R_2$ is $C_1$–$C_3$ alkyl; and X is halogen, preferably chlorine.

In practice, a spirocyclopropanecarboxylic acid ester of formula (II) is reacted with a halogenating agent such as iodobenzene dichloride in the presence of an inert solvent such as chloroform, methylene chloride, dichloroethane and the like at a temperature range of from 20° C. to 30° C. for a period of time sufficient to essentially complete the reaction and obtain the corresponding dihalo derivative (III). This compound is then dehydrohalogenated under anhydrous conditions with an alkali metal alkoxide, such as potassium-t-butoxide in the presence of a solvent such as t-butanol to afford the ester (IV) of the desired monochloro-spirocyclopropanecarboxylic acid. The ester (IV) is hydrolized with a base such as potassium hydroxide in a dilute alcohol to yield the acid (V). This acid is then converted to the acid halide, preferably chloride, with thionyl halide, preferably thionyl chloride in the presence of an inert solvent such as toluene; the acid halide is isolated if so desired, and is then reacted with a benzyl alcohol of formula (VII) in the presence of an acid acceptor such as pyridine and an inert solvent, such as ether to yield the desired insecticide of formula (I).

We find that the compounds represented by formula (I) above are highly effective contact and stomach poisons for a variety of insect pests of crops, particularly Dipterous, Lepidopterous, Coleopterous and Homopterous insects. These compounds are also effective for the control of ectoparasites, especially ixodide ticks, of livestock and domestic animals such as cattle, sheep, horses, dogs, cats and the like.

For the control of insects which attack agricultural crops, the compounds of this invention may be applied to the foliage of the crops, the insect's habitat and/or the insect's food supply in the form of a dilute liquid spray; the compounds may also be applied as a dust, wettable powder, an aerosol or the like.

Dilute, liquid sprays may conveniently be prepared from emulsifiable concentrates. A typical emulsifiable concentrate may comprise about 24% by weight of toxicant; 4% by weight of a surfactant; 23% by weight of a solvent such as cyclohexanone; and about 45% by weight of a petroleum solvent having a minimum aromatic content of about 93 volume %.

The compounds of the invention may also be used as systemic insecticidal-acaricidal agents in the treatment of animals, and as such may be administered to the animals orally or parenterally. When given orally, the active compounds may be formulated as boluses, tablets, capsules or oral drenches; or may be incorporated in an animal feedstuff such as a nutritionally balanced diet containing 0.01% to 3.0% and preferably 0.01% to 1.5% by weight of feed of the active compound.

Systemic insecticidal-acaricidal agents may also be introduced into the body of the animal by subcutaneous, intramuscular or intraperitoneal injection such that it may be distributed through the animal's body by the action of the animal's circulatory system. In practice, the toxicant may be dissolved or dispersed in a pharmaceutically acceptable carrier, such as water, propylene glycol, vegetable oil, glycerol formal, or the like, for administration.

This invention is further demonstrated by the non-limiting examples provided below.

EXAMPLE 1

Preparation of 3'-chloro-3,3-dimethyl-spiro[cyclopropane-1,1'-indene]-2-carboxylic acid, α-cyano-m-phenoxybenzyl ester.

Thionyl chloride (2.0 ml) is added dropwise to a suspension of 3'-chloro-3,3-dimethyl-spiro[cyclopropane-1,1'-indene]-2-carboxylic acid (1.4g; 0.0056 mole) in dry toluene (20 ml) at room temperature. The reaction mixture is warmed briefly to 40° C. then is allowed to stir at room temperature overnight. A dark colored solution forms. The solvent and excess thionyl chloride are then removed in vacuo to afford 1.35 g of acid chloride, a red-brown oil. This acid chloride is dissolved in benzene (20 ml), and added to a solution of α-cyano-m-phenoxybenzyl alcohol (1.25 g; 0.005 mole) and pyridine (0.4 g; 0.0051 mole) in ether at 0 to 10° C. The reaction mixture is then allowed to warm up to room temperature and is stirred overnight. The crude reaction mixture is chromatographed on a dry column (silica gel; 50:50 methylene chloride:hexane), the fractions are combined and evaporated to afford 0.7 g of title product. Elemental Analysis: Calc. C 73.76%; H 4.86%; Cl 7.77%; N 3.07%. Found. C 74,03%; H 4.82%; Cl 10.51%; N 2.81%.

EXAMPLE 2

Preparation of 3'-chloro-3,3-dimethyl-spiro[cyclopropane-1,1'-indene]-2-carboxylic acid, m-phenoxybenzyl ester.

Pyridine (1.68 g) and thionyl chloride (2.5 g) are added to a mixture of 3'-chloro-3,3-dimethyl-spiro[cyclopropane-1,1'-indene]-2-carboxylic acid (5.0 g; 0.02 mole) and ether (50 ml). After two hours at room temperature, pyridine (1.68 g) and m-phenoxybenzyl alcohol (4.0 g) are added and the reaction mixture stirred at room temperature overnight. The reaction mixture is then washed with water, the ether fraction dried over magnesium sulfate and evaporated to dryness. The residue is purified on a dry column (silica gel; 20% methylene chloride:hexane) to afford 3.0 g of title compound, a yellow-orange liquid. The sample is 90–95% pure by NMR, and shows an ester carbonyl stretch at 1730 cm$^{-1}$ in IR.

EXAMPLE 3

Preparation of 3'-chloro-3,3-dimethyl-spiro[cyclopropane-1,1'-indene]-2-carboxylic acid.

A solution of 3'-chloro-3,3-dimethyl-spiro[cyclopropane-1,1'-indene]-2-carboxylic acid ethyl ester (2.0 g; 0.007 mole) in ethanol (10 ml) is added to a mixture of 50% aqueous potassium hydroxide (1.2 ml) and water (1.2 ml), and the mixture is heated at reflux for 1½ hours, then cooled down, diluted with water and extracted with ether. The aqueous phase is then made acid with concentrated hydrochloric acid and extracted with ether. The ethereal extract is washed with water, saturated salt solution, dried over magnesium sulfate and is stripped to afford 1.5 g of title product, a read-brown semisolid.

EXAMPLE 4

Preparation of 3'-chloro-3,3-dimethyl-spiro[cyclopropane-1,1'-indene]-2-carboxylic acid-, ethyl ester.

A solution of 2',3'-dichloro-3,3-dimethyl-spiro[cyclopropane-1,1'-indene]-2-carboxylic acid-, ethyl ester (19 g as is, containing iodobenzene) in t-butanol (50 ml) is added to a 0.1 M solution of potassium-t-butoxide in t-butanol (450 ml; 0.045 mole) and the mixture allowed to stir overnight at room temperature. The reaction mixture is then poured into water, extracted with ether, the ether extracts dried over magsium sulfate and evaporated to dryness to afford 11.1 g of a black oil. This oil is purified by chromatography (silica gel; eluent: 1:1 mixture of methylene chloride:hexane), to afford 2 g of title product, a yellow oil.

EXAMPLE 5

Preparation of 2',3'-dichloro-3,3-dimethyl-spiro[cyclopropane-1,1'-indene]-2-carboxylic acid-, ethyl ester.

To a stirred solution of 3,3-dimethyl-spiro[cyclopropane-1,1'-indene]-2-carboxylic acid ethyl ester (7.3 g; 0.03 mole) in chloroform (100 ml) is added iodobenzene dichloride (8.3 g; 0.03 mole) in small increments. Incomplete solution occurs. The reaction mixture is stirred overnight at room temperature, after which time a clear solution forms. The solution is stripped in vacuo at 50°–60° C. to leave 15.4 g of a residual oil comprising a mixture of the title product and iodobenzene as indicated by NMR.

EXAMPLE 6

Preparation of iodobenzene dichloride.

Chlorine gas is bubbled through a solution of iodobenzene (20.4 g; 0.1 mole) in chloroform (100 ml) while the temperature of the reaction mixture is maintained at −5° C. In about 10 minutes a yellow solid precipitates and is removed by filtration. The filtrate is then further treated with chlorine gas until the formation of yellow solid ceases. The solid fractions are combined and air dried to afford 25.9 g (94.2%) of title product.

EXAMPLE 7

Evaluation of the test compounds for the control of Ixodidae.

The efficacy of the compounds of the invention for control of ticks is demonstrated in the following tests wherein engorged adult female *Boophilus microplus*, multiple resistant strain, ticks which have dropped from cattle are collected and used for testing.

The compound to be tested is dissolved in a 35% acetone/65% water mixture in amounts sufficient to provide the concentrations indicated in Table I below. Ten ticks per treatment are used and they are immersed in the test solution for three to five minutes, then removed and held in incubators for two to three weeks at 28° C. Counts of ticks laying eggs are then made and recorded. Eggs which were laid are placed in containers and kept for one month to observe hatching and to determine chemosterilant effect. Results of these tests are given in Table I below.

Percent reduction in viable egg masses is believed to be indicative of one or more of the following mechanisms:
1. Killing of the tick.
2. Suppression of fecundity.
3. Chemosterilant effect.

EXAMPLE 8

Evaluation of the efficacy of the compounds of the invention for the control of *Boophilus microplus* larvae.

Effective control of acarina larvae is demonstrated in the following tests with larvae of *Boophilus microplus*, a one-host tick which can remain on a single host through its three life stages, i.e. larva, nymph and adult. In these tests a 10% acetone/90% water mixture contains the test compound at the concentrations indicated in Table II below. Twenty larvae are enclosed in a pipet sealed at one end with a gauze material, and a solution, containing the test compound at the concentrations given, is then drawn through the pipet with a vacuum hose simulating a spray system. The ticks are then held for 48 hours at room temperature, and percent mortality rates are then determined. The results obtained with the various compounds are tabulated in Table II below.

TABLE I

Evaluation of the Test Compounds for the Control of Ixodidae

| Compound | Concentration in ppm | Percent reduction in viable egg masses |
|---|---|---|
| [structure: dimethylcyclopropane-indene-Cl with C(=O)-O-CH(CN)-phenyl-O-phenyl] | 125 | 98 |
| [structure: dimethylcyclopropane-indene-Cl with C(=O)-O-CH₂-phenyl-O-phenyl] | 125 | 91.9 |
|  | 62 | 83.9 |
|  | 31 | 72.7 |
|  | 15 | 0 |

TABLE II

Efficacy of the compounds of the invention for the control of *Boophilus microplus* larvae.

| Compound | Concentration in ppm | Percent Mortality of *Boophilus microplus* |
|---|---|---|
| [structure: dimethylcyclopropane-indene-Cl with C(=O)-O-CH(CN)-phenyl-O-phenyl] | 0.78 | 80–100 |
|  | 0.19 | 80 (O)* |
|  | 0.05 | 0 |
|  | 0.012 | 0 |
| [structure: dimethylcyclopropane-indene-Cl with C(=O)-O-CH₂-phenyl-O-phenyl] | 100 | 100 |

*Two replicates, one 80%, the other 0% control.

EXAMPLE 9

Insecticide testing procedures.

Malaria Mosquito (*Anopheles quadrimaculatus* say) egg and larvae test.

One ml of a 300 ppm solution is pipetted into a 400 ml beaker containing 250 ml of deionized water and stirred with the pipette, giving a concentration of 1.2 ppm. A wax paper ring 0.6 cm wide to fit inside the beaker is floated on the surface of the test solution to keep the eggs from floating up the meniscus curve and drying out on the side of the glass. A spoon made of screen in used to scoop up and transfer about 100 eggs (0-24 hours old) into the test beaker. After two days at 26.7° C. observations of hatching are made. This includes kill of eggs or inhibition of hatch, kill of newly hatched larvae, or delayed hatch. Additional observations are made after another day for the same effects.

Tobacco Budworm [*Heliothis virescens* (Fabricius)].

A cotton plant with 2 true leaves expanded is dipped for 3 seconds with agitation in a 300 ppm solution. A 1.25 to 2 cm square of cheesecloth with about 50 to 100 budworm eggs 0-24 hours old is also dipped in the test solution and placed on one leaf to dry. The leaf with the treated budworm eggs is removed from the plant and placed in a 236.6 ml (8-oz.) Dixie cup with a wet 5 cm piece of dental wick and covered with a lid. The other leaf is placed in a similar cup with a wick and a piece of cheesecloth infested with 50-100 newly hatched larvae is added before covering the cup with a lid. After 3 days at 26.7° C., observation of egg hatch are made as well as kill of newly hatched larvae, any inhibition of feeding, or interference of any sort with normal development.

Phosphate-Resistant Strain of Two-Spotted Spider Mite

[*Tetranychus urticae* (Koch)].

Sieva lima bean plants, with primary leaves 7.6 to 10 cm long, are infested with about 100 adult mites per leaf 4 hours before use in this test, in order to allow egg-laying before treatment. The infested plants are dipped for 3 seconds with agitation into a 300 ppm solution, and the plants set in the hood to dry. After 2 days at 26.7° C., the adult mite mortality is estimated on one leaf under a 10X stereoscopic microscope. The other leaf is left on the plant an additional 5 days and then examined at 10X power to estimate the kill of eggs and of newly-hatched nymphs, giving a measure of ovicidal and residual action, respectively.

Southern Armyworm [*Spodoptera eridania* (Cramer)].

A Sieva lima bean plant with just the primary leaves expanded to 7.6 to 10 cm is dipped for 3 seconds with agitation in a 1000 ppm solution and set in a hood to dry. Following this, one leaf is placed in a 10 cm petri dish which has a moist filter paper in the bottom and 10 third-instar armyworm larvae about 1 cm long. The dish is covered and held at 26.7° C. After 2 days mortality counts and estimates of the amount of feeding are made. Compounds showing partial kill and/or inhibition of feeding are held for an extra day for further observations.

All compounds showing activity as defined above are retested, using the second leaf on the bean plant, after an interval of 7 days from original treatment, as an assay of residual activity.

Mexican Bean Beetle (*Epilachna varivestis* Mulsant)

Sieva lima bean plants (2 per pot) with primary leaves 7.6 to 10 cm long, are dipped in a 300 ppm solution and set in a hood to dry. One leaf is removed from the plant and placed in a 10 cm petri dish containing a moist filter paper on the bottom and 10 last-instar larvae (13 days from hatching).

The day after treatment, another leaf is removed from the plant and fed to the larvae after removing the remains of the original leaf. Two days after treatment, the third leaf is fed to the larvae, this usually being the last needed. The fourth leaf is used on the third day after treatment if the larvae have not finished feeding. The test is now set aside and held until adults have emerged, usually about 9 days after treatment began. After emergence is complete, each dish is examined for dead larvae, pupae or adults; deformed pupae or adults; larval-pupal intermediates or pupal-adult intermediates; or any other interference with normal molting, transformation and emergence of pupae or adults.

Western Potato Leaf Hopper (*Empoasca abrupta* DeLong)

A lima bean plant with the primary leaf expanded to 7.6 to 10 cm is dipped into a 100 ppm solution and set in a hood to dry. A 2.5 cm piece of the tip of 1 leaf is cut off and placed in a 10 cm petri dish with a moist filter paper in the bottom. (In practice, this is usually cut off the tip of a plant from the Mexican bean beetle tests using a bean leaf dipped in the needed solution). From 3 to 10 second-instar nymphs are tapped from the culture plants into the test dish and rapidly covered. Mortality counts are made after two days at 26.7° C.

Malaria Mosquito (*Anopheles quadrimaculatus* Say)

Adult Test.

Ten ppm solutions are poured into wide-mouth 46.2 ml jars each containing a microscope slide. The slides are removed from the test solution with forceps and laid horizontally to dry on a wide-mouth 118.4 ml bottle. When dry, they are placed in the same 118.4 ml bottle and ten 4 to 5-day old mosquitoes of mixed sexes are added to each bottle. A piece of cotton gauze held on by an elastic band serves as a lid and a wad of cotton soaked in 10% honey solution serves as food. Mortality counts are made after 1 day at 26.7° C.

Bean Aphid (*Aphid fabae* Scopoli).

Five cm fiber pots, each containing a nasturtium plant 5 cm high and infested with 100 to 500 aphids 2 days earlier are placed on a 4 rpm turntable and sprayed with a 100 ppm solution for 2 revolutions with a No. 154 DeVilbiss Atomizer at 1.4 kg/cm$^2$ air pressure. The spray tip is held about 15 cm from the plants and the spray directed so as to give complete coverage of the aphids and the plants. The sprayed plants are laid on their sides on white enamel trays. Mortality estimates are made after 1 day at 26.7° C.

Tobacco Budworm [*Heliothis virescens* (Fabricius)].

Third instar.

Three cotton plants with just expanded cotyledons are dipped in a 1000 ppm solution, and placed in a hood to dry. When dry, each cotyledon is cut in half and 10 are each placed in a 29.6 ml plastic medicine cup containing a 1.25 cm dental wick saturated with water, and one third-instar budworm larva is added. The cup is capped and held for 3 days at 26.7° C., after which mortality counts are made.

Cabbage Looper. [*Trichoplusia ni* (Hubner)].

A primary leaf of a cotton plant is dipped in the test solution and agitated for 3 seconds. It is then set in a hood to dry. Following this, the leaf is placed in a 10 cm petri dish containing a moist filter paper at the bottom and 10 third-instar loopers. The dish is covered and held at 26.7° C. After 2 days, mortality counts and estimates of feeding damage are recorded. Those materials showing partial kill and/or inhibition of feeding are held for another day for further observations.

The rating system employed in these tests is as follows:

Rating System

0 = 0–40% killed or affected
1 = reduced feeding (trace to light damage)
2 = some deformed insects (40–80%)
3 = mostly deformed insects (85–100%)
4 = not an index number at present
5 = 51–60% mortality
6 = 61–70% mortality
7 = 71–85% mortality
8 = 86–95% mortality
9 = 100% mortality The absence of a number indicates that no test has been run at that particular dosage.

Compounds rated active (8 or 9) are further tested at reduced concentrations in 50% acetone:50% water.

Data obtained are reported in Table III below.

TABLE III

Evaluation of the Insecticidal Activity of the Compounds of the Invention.

| Structure | Mosquito Larvae ppm | | | Tobacco Budworm | | | | | |
|---|---|---|---|---|---|---|---|---|---|
| | | | | Eggs - ppm | | | Larvae - ppm | | |
| | 1.2 | 0.4 | 0.04 | 300 | 100 | 10 | 300 | 100 | 10 |
| (structure 1) | 9 | 9 | 9 | 0 | | | 9 | 9 | 9 |
| (structure 2) | 9 | 9 | 9 | 0 | | | 9 | 9 | 9 |

TABLE IIIb

Evaluation of the Insecticidal Activity of the Compounds of the Invention.

| Structure | Phosphate Resistant Mites ppm | | | Southern Armyworms ppm | | | | Mexican Bean Beetles ppm | | |
|---|---|---|---|---|---|---|---|---|---|---|
| | 300 | 100 | 10 | 1000 | 100 | 10 | 7-days | 300 | 100 | 10 |
| (structure 1) | 8 | 5 | 0 | 9 | 9 | 7 | 0 | 9 | 9 | 9 |
| (structure 2) | 8 | 0 | | 9 | 9 | 0 | | 9 | | |

TABLE IIIc
Evaluation of the Insecticidal Activity of the Compounds of the Invention.

| Structure | Leaf Hopper ppm | | Mosquito, Adult ppm | | Bean Aphids ppm | | | Tobacco Budworm 3rd Instar-ppm | | Cabbage Looper ppm | |
|---|---|---|---|---|---|---|---|---|---|---|---|
| | 100 | 10 | 10 | 1 | 100 | 10 | 1 | 1000 | 100 | 1000 | 100 |
| 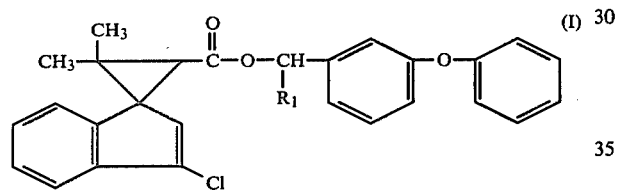 | 9 | 9 | 9 | 7 6 9 | 9 | 9 | 9 | 5 | 0 | 9 | 9 |
| 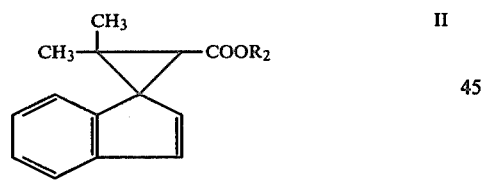 | 9 | 9 | 0 | | 9 | 9 | 0 | 9 | 5 | 9 | 9 |

I claim:
1. A method for preparing compounds of the formula:

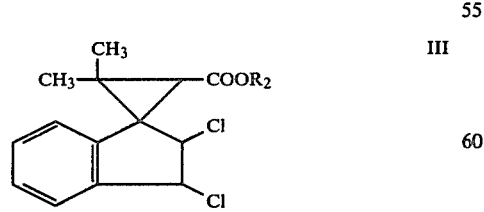

wherein R₁ is hydrogen or cyano which comprises reacting a spirocyclopropanecarboxylic acid ester of the formula

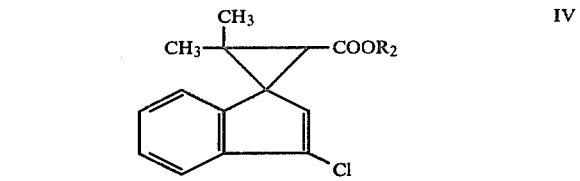

wherein R₂ is C₁–C₃ alkyl with a halogenating agent in the presence of an inert solvent at a temperature in the range of from 20° C. to 30° C. for a period of time to essentially complete the reaction and obtain the dihalo derivative of the formula

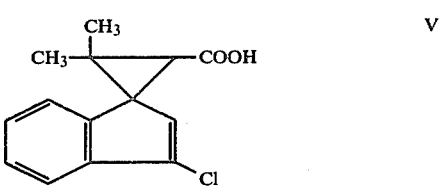

dehydrohalogenating the dihalo derivative III under anhydrous conditions with an alkali metal alkoxide in the presence of a solvent to produce the ester

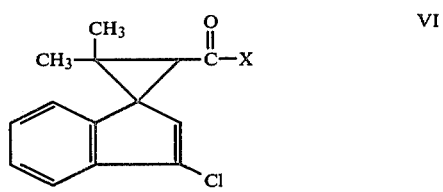

hydrolizing the ester IV with a base in a dilute alcohol to yield the acid

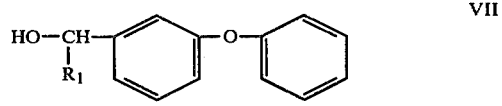

converting the acid V to the acid halide wherein X is halogen by reacting acid V with a thionyl halide in the presence of an inert solvent isolating the acid halide VI and then reacting the acid halide VI with a benzyl alcohol in the presence of an acid acceptor and an inert solvent to yield the compound of formula I.

* * * * *